US012667727B2

(12) United States Patent
Chang et al.

(10) Patent No.: US 12,667,727 B2
(45) Date of Patent: Jun. 30, 2026

(54) ELECTRICAL STIMULATION METHOD, ELECTRICAL STIMULATION DEVICE, AND COMPUTER-READABLE STORAGE MEDIUM

(71) Applicant: GIMER MEDICAL. Co. LTD., New Taipei City (TW)

(72) Inventors: Chi-Heng Chang, New Taipei City (TW); Jian-Hao Pan, New Taipei City (TW)

(73) Assignee: COFORCE MEDICAL CO., LTD., Taipei City (TW)

( * ) Notice: Subject to any disclaimer, the term of this patent is extended or adjusted under 35 U.S.C. 154(b) by 504 days.

(21) Appl. No.: 17/979,297

(22) Filed: Nov. 2, 2022

(65) Prior Publication Data

US 2023/0201601 A1     Jun. 29, 2023

(30) Foreign Application Priority Data

Dec. 29, 2021    (CN) .......................... 202111638878.4

(51) Int. Cl.
*A61N 1/36*            (2006.01)

(52) U.S. Cl.
CPC ....... *A61N 1/3614* (2017.08); *A61N 1/36171* (2013.01); *A61N 1/36175* (2013.01)

(58) Field of Classification Search
None
See application file for complete search history.

(56) References Cited

U.S. PATENT DOCUMENTS

| | | | |
|---|---|---|---|
| 5,003,975 A | | 4/1991 | Hafellinger et al. |
| 5,999,852 A | * | 12/1999 | Elabbady ........... A61N 1/39046 607/8 |
| 2003/0229379 A1 | * | 12/2003 | Ramsey, III ......... A61N 1/3918 607/5 |
| 2006/0247683 A1 | * | 11/2006 | Danek ................... A61N 1/403 607/2 |
| 2011/0098765 A1 | * | 4/2011 | Patel ................... A61N 1/3925 607/28 |

(Continued)

FOREIGN PATENT DOCUMENTS

| | | |
|---|---|---|
| CN | 111655325 A | 9/2020 |
| CN | 113811255 A | 12/2021 |

(Continued)

OTHER PUBLICATIONS

Extended European Search Report for European Application No. 22215616.8, dated May 22, 2023.

(Continued)

*Primary Examiner* — Benjamin J Klein
*Assistant Examiner* — Willow Grace Welch
(74) *Attorney, Agent, or Firm* — Birch, Stewart, Kolasch & Birch, LLP

(57)             ABSTRACT
An electrical stimulation method is provided. The electrical stimulation method is applied to an electrical stimulation device. The steps of the electrical stimulation method include obtaining a target energy value; providing an electrical stimulation signal to a target area; calculating a total energy value according to an energy value transmitted from the electrical stimulation signal to the target area; and determining whether the total energy value has reached the target energy value.

28 Claims, 9 Drawing Sheets

900

(56)                  References Cited

U.S. PATENT DOCUMENTS

| | | | | |
|---|---|---|---|---|
| 2012/0197331 A1* | 8/2012 | Germanson | .......... | A61N 1/3706 |
| | | | | 607/11 |
| 2012/0290039 A1 | 11/2012 | Moffitt et al. | | |
| 2016/0045735 A1* | 2/2016 | Chang | .................. | A61N 1/0551 |
| | | | | 607/46 |
| 2016/0228178 A1* | 8/2016 | Lei | ........................... | A61N 1/06 |
| 2021/0361194 A1* | 11/2021 | Arab | ...................... | A61N 1/025 |
| 2023/0146947 A1* | 5/2023 | Shelton, IV | ....... | A61B 17/1285 |
| | | | | 606/144 |

FOREIGN PATENT DOCUMENTS

| | | | |
|---|---|---|---|
| TW | 201338543 A | 9/2013 | |
| WO | WO 2012/148401 A1 | 11/2012 | |

OTHER PUBLICATIONS

Taiwanese Office Action and Search Report for Taiwanese Application No. 111130859, dated Feb. 3, 2023.

* cited by examiner

321

322

100

| electrical stimulation level | L1 | L2 | L3 | L4 | L5 | L6 | L7 | L8 | L9 | L10 |
|---|---|---|---|---|---|---|---|---|---|---|
| first target energy set | X1 | X2 | X3 | X4 | X5 | L6 | X7 | X8 | X9 | X10 | predetermined electrical stimulation level target energy upper bound target energy lower bound

FIG. 5A

| electrical stimulation level | L1 | L2 | L3 | L4 | L5 | L6 | L7 | L8 |
|---|---|---|---|---|---|---|---|---|
| second target energy set | Y1<br>=<br>X5 | Y2 | Y3 | Y4 | Y5 | Y6 | Y7 | Y8<br>=<br>X8 |

ELECTRICAL STIMULATION METHOD, ELECTRICAL STIMULATION DEVICE, AND COMPUTER-READABLE STORAGE MEDIUM

CROSS REFERENCE TO RELATED APPLICATIONS

This application claims priority of China Patent Application No. 202111638878.4, filed on Dec. 29, 2021, the entirety of which is incorporated by reference herein.

BACKGROUND

Technology Field

The present disclosure relates in general to electrical stimulation techniques.

Description of the Related Art

In recent years, dozens of kinds of therapeutic electrical nerve stimulation devices have been developed, and tens of thousands of people needing electrical stimulation devices undergo implant surgery every year. Due to developments in precision manufacturing technology, medical instruments such as implantable electrical stimulation devices have been shrunk so that they can be implanted into the human body.

A conventional electrical stimulation device generally performs electrical stimulation 24 hours a day, until there is no electricity remaining. When it is necessary to change the electrical stimulation parameters of the electrical stimulation signal, only the pulse width of the electrical stimulation signal and the amplitude of the signal (that is, the magnitude of the voltage or current) can be adjusted. There is no specific relationship between the pulse width and the electrical stimulation parameters such as voltage and current. Therefore, setting the electrical stimulation parameters is usually left to the doctor's choice, based on personal and professional experience.

SUMMARY

In view of the problems of the prior art described above, an electrical stimulation method, an electrical stimulation device, and a computer-readable storage medium are provided in the embodiments of the present disclosure.

An embodiment of the present disclosure provides an electrical stimulation method. The electrical stimulation method is applied to an electrical stimulation device. The steps of the electrical stimulation method comprise: obtaining a target energy value; providing an electrical stimulation signal to a target area; calculating a total energy value according to an energy value transmitted from the electrical stimulation signal to the target area; and determining whether the total energy value has reached the target energy value.

An embodiment of the present disclosure provides an electrical stimulation device. The above-mentioned electrical stimulation device comprises an electrical stimulation signal generation circuit and a calculation module. The electrical stimulation signal generation circuit provides an electrical stimulation signal to a target area. The calculation module obtains a target energy value, calculates a total energy value according to an energy value of the electrical stimulation signal transmitted to the target area, and determines whether the total energy value has reached the target energy value.

An embodiment of the present disclosure provides a computer-readable storage medium. The computer-readable storage medium stores one or more instructions and cooperates with an electrical stimulation device. When the one or more instructions are executed by the electrical stimulation device, the electrical stimulation device executes a plurality of steps, comprising: obtaining a target energy value; providing an electrical stimulation signal to a target area; calculating a total energy value according to an energy value of the electrical stimulation signal transmitted to the target area; and determining whether the total energy value has reached the target energy value.

It will be apparent to those skilled in the art that various modifications and variations can be made in the present disclosure, without departing from the spirit and scope of the present disclosure.

BRIEF DESCRIPTION OF THE DRAWINGS

The present disclosure can be more fully understood by reading the subsequent detailed description and examples with references made to the accompanying drawings, wherein:

FIG. 5A illustrates the first target energy set, according to an embodiment of the present disclosure;

FIG. 5B illustrates the second target energy set, according to an embodiment of the present disclosure;

DETAILED DESCRIPTION OF THE INVENTION

The following description is a preferred embodiment of the invention, which is intended to describe the basic spirit of the invention, but is not intended to limit the invention. For the actual inventive content, reference must be made to the scope of the claims.

Figure 1:
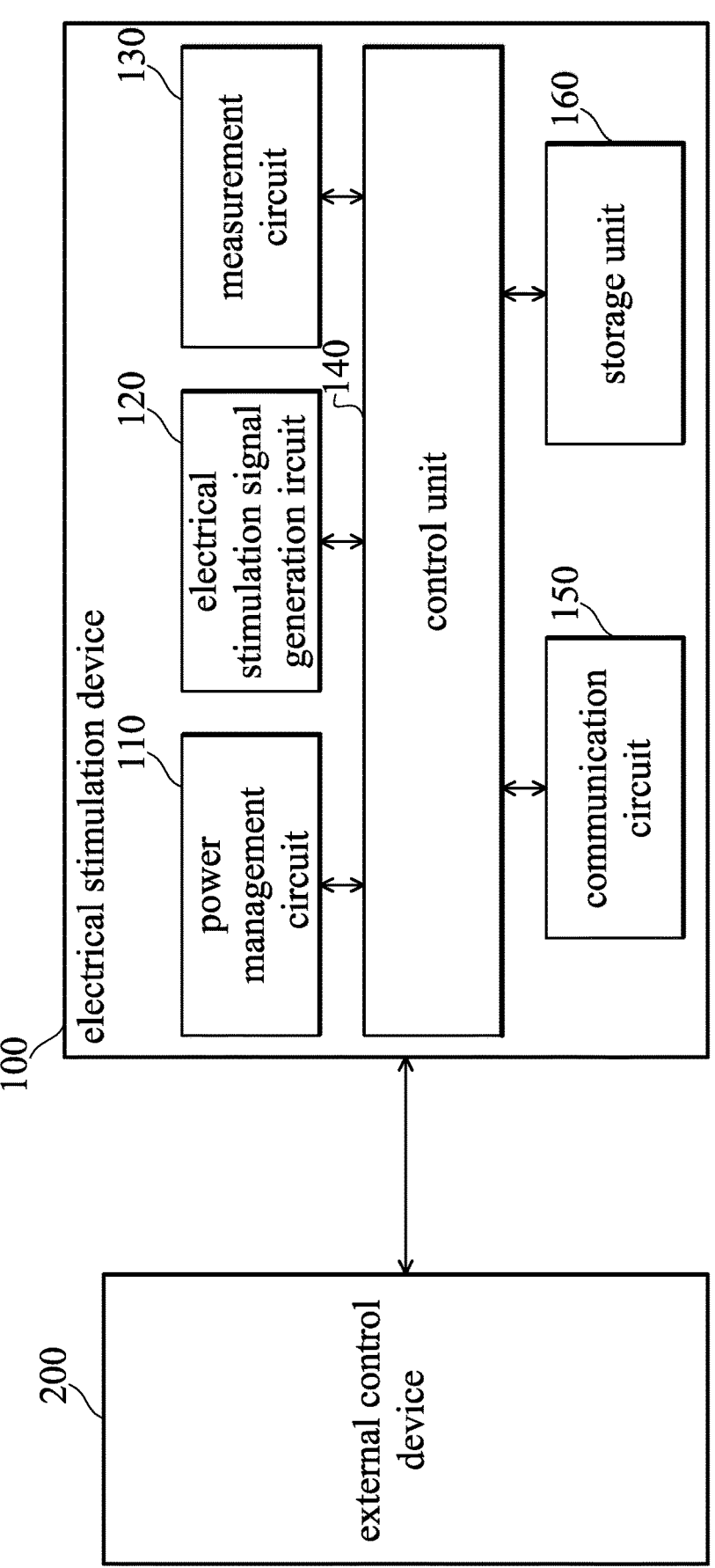
FIG. 1 is a block diagram of an electrical stimulation device, according to an embodiment of the present disclosure.

FIG. 1 is a block diagram of an electrical stimulation device 100, according to an embodiment of the present disclosure. As shown in FIG. 1, the electrical stimulation device 100 at least includes a power management circuit 110, an electrical stimulation signal generation circuit 120, a measurement circuit 130, a control unit 140, a communication circuit 150, and a storage unit 160. It should be appreciated that the block diagram shown in FIG. 1 is only for the convenience of explaining the embodiments of the present disclosure, the present disclosure is not limited thereto. The electrical stimulation device 100 may also include other elements.

According to an embodiment of the present disclosure, the electrical stimulation device 100 may be electrically coupled to an external control device 200. The external control device 200 may be provided with an operation interface. According to user's operation on the operation interface, the external control device 200 may generate instructions or signals to be transmitted to the electrical stimulation device 100, and transmits the instructions or signals to the electrical stimulation device 100 via a wire communication (e.g., a transmission line).

In addition, according to another embodiment of the present disclosure, the external control device 200 may transmit the instructions or signals to the electrical stimulation device 100 via a wireless communication, such as Bluetooth, Wi-Fi, or NFC (near field communication).

According to the embodiment of the present disclosure, the electrical stimulation device 100 may be an implantable electrical stimulation device, an external electrical stimulation device with a lead implanted into human body, or a transcutaneous electrical stimulation device (TENS). According to an embodiment of the present disclosure, when the electrical stimulation device 100 is a non-implantable electrical stimulation device (e.g., an external electrical stimulation device or a transcutaneous electrical stimulation device), the electrical stimulation device 100 may be integrated with the external control device into a device. According to an embodiment of the present disclosure, the electrical stimulation device 100 may be an electrical stimulation device with batteries, or an electrical stimulation device of which power is transmitted wirelessly by the external control device 200. According to an embodiment of the present disclosure, in a trial phase, the electrical stimulation device 100 is an external electrical stimulation device with a lead implanted into human body. There are electrodes on the lead, so that the external electrical stimulation device may send the electrical stimulation signal to the corresponding target area via the electrodes on the lead. In the trial phase, after the terminal of the lead with an electrode has been implanted into the human body, the other terminal is thereby linked to the external control device 200, and the external stimulation device may send an electrical stimulation signal to evaluate the effectiveness of the therapy, and to confirm if the functions of the lead are normal, and if the position into which the lead is implanted is correct. In the trial phase, the external control device 200 may first pair with the external electrical stimulation device (i. e., a non-implantable electrical stimulation device). After the lead is implanted into the human body, the external electrical stimulation device may be connected to the lead. The external electrical stimulation device may be wirelessly controlled by the external control device 200 to perform electrical stimulation of the human body. According to an embodiment of the present disclosure, if the evaluation in the trial phase is effective, a permanent implantation phase may be entered. In the permanent implantation phase, the electrical stimulation device 100 is implanted into the human body together with the lead. The electrical stimulation device 100 sends the electrical signal to the corresponding target area via the electrodes on the lead. While the external control device 200 is entering the permanent implantation phase, a user or a doctor must let the external control device 200 detect a phase change card, so as to change the state of the external control device 200 from the trial phase to the permanent implantation phase via near field wireless communication. In addition, the external control device 200 may select a target energy upper bound and a target energy lower bound from the first target energy set according to a predetermined electrical stimulation level. Then, the external control device 200 may generate the second target energy set according to the target energy upper bound and the target energy lower bound (further explanation will be provided). Moreover, before the permanent implantation phase or during the permanent implantation phase, the external control device 200 may pair with the implantable electrical stimulation device first, and the external electrical stimulation device (i.e., a non-implantable electrical stimulation device) may be removed, and the electrical stimulation device 100 (i.e., an implantable electrical stimulation device) connects to the lead and is implanted into the human body.

According to the embodiment of the present disclosure, the power management circuit 110 is used for providing power to the elements and circuit in the electrical stimulation device 100. The power provided by the power management circuit 110 may be from a built-in rechargeable battery, or the external control device 200, but the present disclosure is not limited thereto. The external control device 200 may provide power to the power management circuit 110 using a wireless power technology. The power management circuit 110 may be activated or deactivated according to the instructions of the external control device 200. According to an embodiment of the present disclosure, the power management circuit 110 may include a switch circuit (not shown in the figure). The switch circuit may be switched on or off according to the instructions of the external control device 200, so as to activate or deactivate the power management circuit 110.

According to the embodiment of the present disclosure, the electrical stimulation signal generation circuit 120 is used for generating the electrical stimulation signal. The electrical stimulation device 100 may transmit the generated electrical stimulation signal to the electrodes on the lead via at least a lead, so as to perform electrical stimulation on the target area of the body of a user (human or animal) or a patient. The target area may be, for example, spine, spinal nerve, vagus nerve, trigeminal nerve, lateral recess, or peripheral nerve, but the present disclosure is not limited thereto. The detailed structure regarding the electrical stimulation signal generation circuit 120 will be explained in FIG. 4.

Figure 2A:
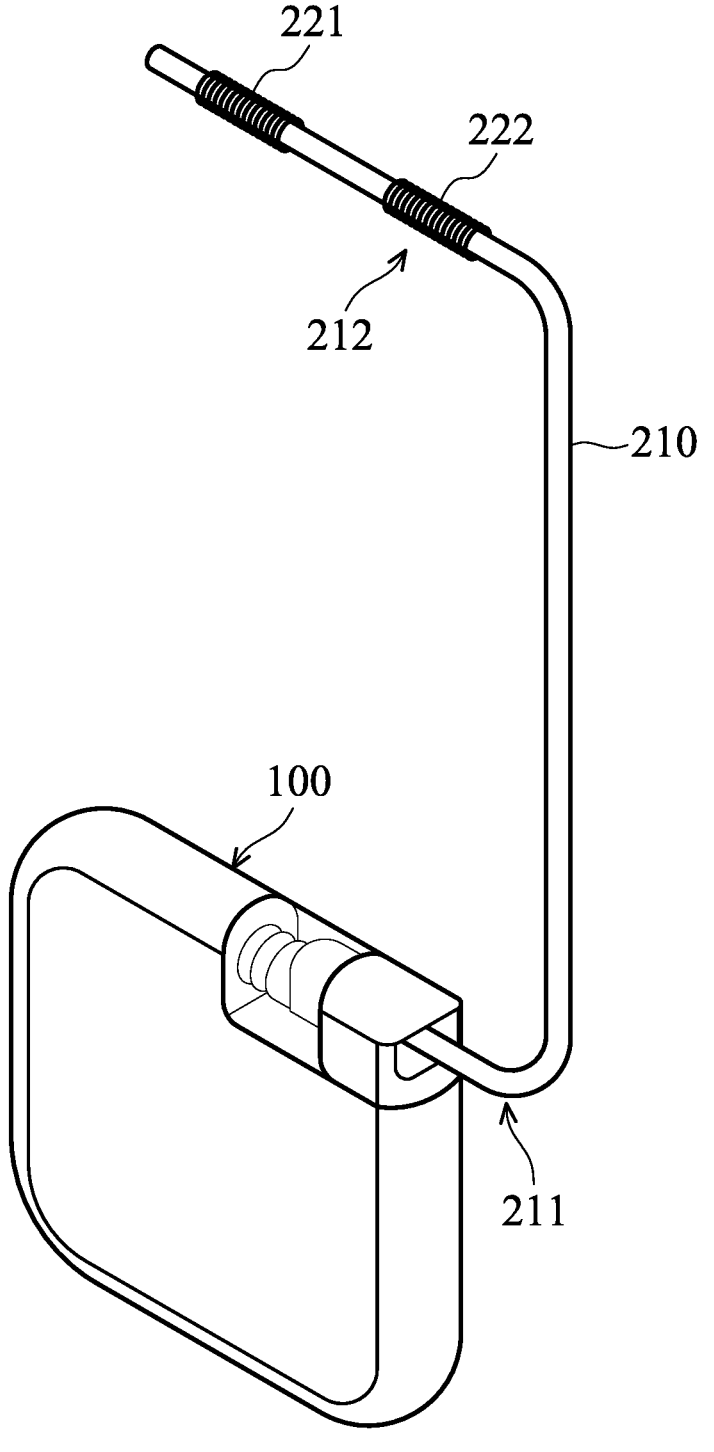
FIG. 2A is a schematic diagram of an electrical stimulation device, according to an embodiment of the present disclosure.

FIG. 2A is the schematic diagram of an electrical stimulation device 100, according to an embodiment of the present disclosure. As shown in FIG. 2A, the electrical stimulation signal may be output to the lead 210, so that the electrical stimulation signal may be transmitted via a terminal 211 of the lead 210 to the other terminal 212 of the lead 210. In an embodiment of the present disclosure, the electrical stimulation device 100 and the lead 210 may be separately electrically connected to each other, but the present disclosure is not limited thereto. For example, the electrical stimulation device 100 and the lead 210 may be a monolithic device.

Figure 2B:
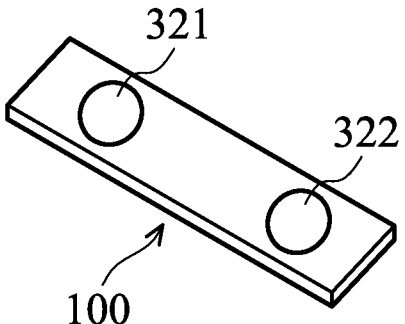
FIG. 2B is a schematic diagram of an electrical stimulation device, according to another embodiment of the present disclosure.

FIG. 2B is the schematic diagram of an electrical stimulation device 100, according to another embodiment of the present disclosure. As shown in FIG. 2B, the electrode 321 and the electrode 322 may be directly installed on one side of the electrical stimulation device 100. The electrical stimulation signal may be transmitted to the electrode 321 or the electrode 322, so as to perform electrical stimulation on the target area. In other words, in this embodiment, the electrical stimulation device 100 does not need to transmit the electrical stimulation signal to the electrode 321 and the electrode 322 via the lead.

Figure 3:
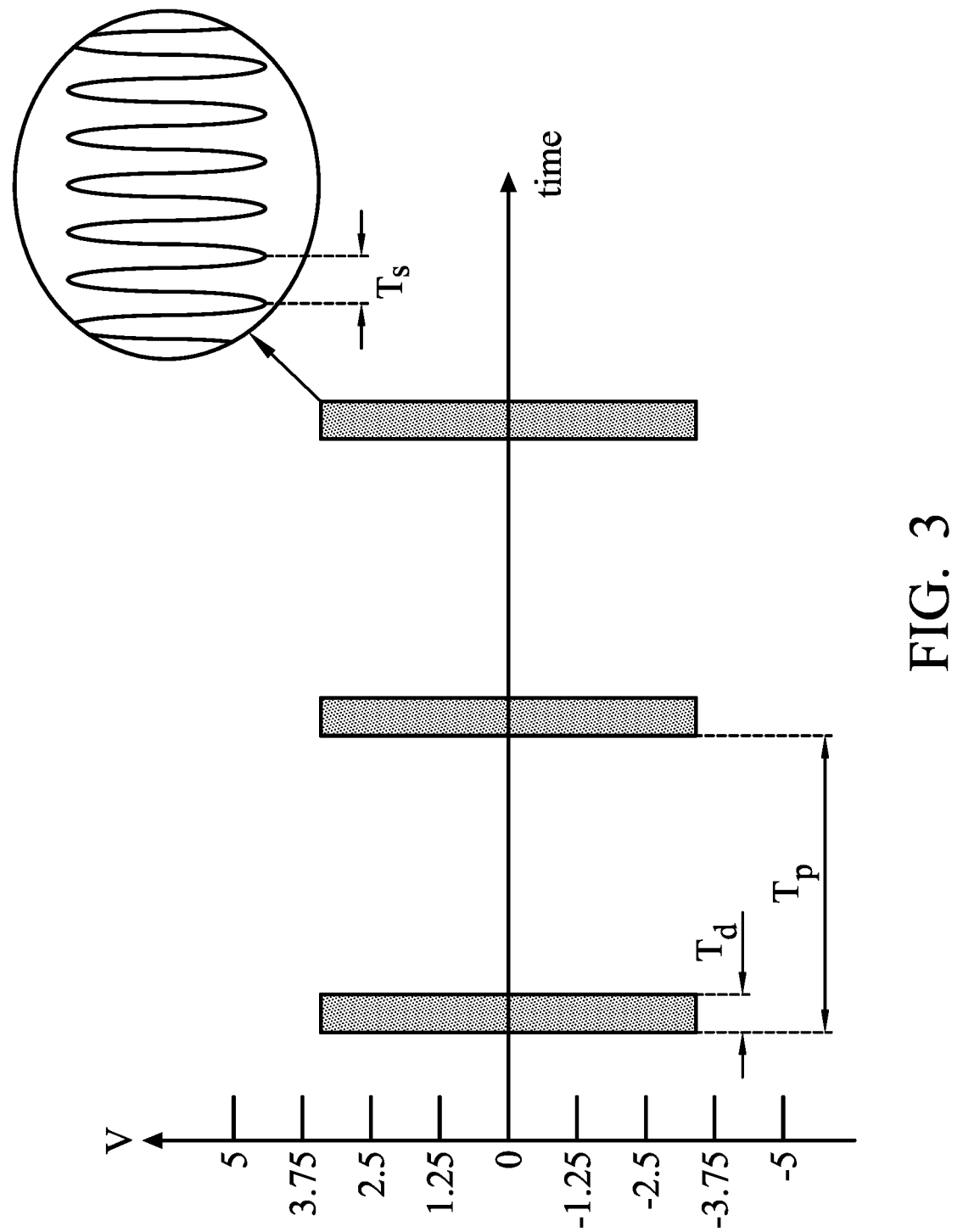
FIG. 3 is a waveform diagram of the electrical stimulation signals of the electrical stimulation device, according to an embodiment of the present disclosure.

FIG. 3 is the waveform diagram of the electrical stimulation signals of the electrical stimulation device, according to an embodiment of the present disclosure. As shown in FIG. 3, according to an embodiment of the present disclosure, the electrical stimulation signal may be a pulsed radiofrequency (PRF) signal (also referred to as a pulse signal, for short), a continuous sinusoidal waveform, or a continuous triangle waveform, but the present disclosure is not limited thereto. Besides, when the electrical stimulation signal is a pulse AC (alternating current) signal, a pulse cycle time $T_p$ includes a pulse signal and at least an idle period, and the pulse cycle time $T_p$ is the inverse of the pulse repetition frequency. For example, the pulse repetition frequency (also referred to as the pulse frequency, for short) may ranges from 0 Hertz to 1K Hertz, preferably range from 1 Hertz to 100 Hertz. In this embodiment, the exemplary pulse repetition frequency of the electrical stimulation signal is 2 Hertz. Besides, the duration time $T_d$ (i.e., the pulse width) of a pulse in a pulse cycle time may be at 1-250 milliseconds, preferably at 10-100 milliseconds. In this embodiment, the exemplary duration time $T_d$ is 25 milliseconds. In this embodiment, the frequency of the electrical stimulation signal is 500K Hertz. In other words, the electrical stimulation signal cycle time $T_s$ is approximately 2 microseconds($\mu$ s). In addition, the frequency of the electrical stimulation signal is the intra-pulse frequency in each pulse AC signal of FIG. 3. In some embodiments, the intra-pulse frequency of the electrical stimulation signal may, for example, range from 1K Hertz to 1000K Hertz. It should be appreciated that in each embodiment of the present disclosure, the frequency of the electrical stimulation signal refers to the intra-pulse frequency of the electrical stimulation signal. Furthermore, the intra-pulse frequency of the electrical stimulation signal may, for example, range from 200K Hertz to 800K Hertz. Furthermore, the intra-pulse frequency of the electrical stimulation signal may, for example, range from 480K Hertz to 850K Hertz. Furthermore, the intra-pulse frequency of the electrical stimulation signal may be, for example, 500K Hertz. The voltage of the electrical stimulation signal may range from −25V~+25V. Furthermore, the voltage of the electrical stimulation signal may range from −20V~+20V. The current of the electrical stimulation signal may range from 0-60 mA. Furthermore, the current of the electrical stimulation signal may range from 0-50 mA.

According to an embodiment of the present disclosure, a user may operate the electrical stimulation device 100 to perform electrical stimulation only when in need (e.g., the symptom becomes more serious or does not alleviate). After the electrical stimulation device 100 has performed electrical stimulation on the target area once, the electrical stimulation device 100 must wait for a limited period before performing electrical stimulation on the target area again. For example, after the electrical stimulation device 100 has performed electrical stimulation on the target area once, the electrical stimulation device 100 must wait for 30 minutes (i.e., the limited period) before performing electrical stimulation on the target area again, but the present disclosure is not limited thereto. The limited period may be 45 minutes, 1 hour, 4 hours, or any time period within 24 hours.

According to the embodiment of the present disclosure, the measurement circuit 130 may measure the voltage value and the current value of the electrical stimulation signal according to the electrical stimulation signal generated by the electrical stimulation signal generation circuit 120. In addition, the measurement circuit 130 may measure the voltage value and the current value on the tissues in the target area of the body of the user or the patient. According to an embodiment of the present disclosure, the measurement circuit 130 may adjust the current and the voltage of the electrical stimulation signal according to the instructions of the control unit 140. The detailed structure regarding the measurement circuit 130 will be explained in FIG. 4.

According to the embodiment of the present disclosure, the control unit 140 may be a controller, a microcontroller, or a processor, but the present disclosure is not limited thereto. The control unit 140 may be used for controlling the electrical stimulation signal generation circuit 120 and the measurement circuit 130. The operations regarding the control unit 140 will be explained in FIG. 4.

According to the embodiment of the present disclosure, the communication circuit 150 may be used for communicating with the external control device 200. The communication circuit 150 may transmit the instructions or signals received by the external control device 200 to the control unit 140, and transmit the data measured by the electrical stimulation device 100 to the external control device 200. According to the embodiment of the present disclosure, the communication circuit 150 may be a wireless communication or a wire communication for communicating with the external control device 200.

According to an embodiment of the present disclosure, all the electrodes of the electrical stimulation device 100 may be activated during the electrical stimulation. Therefore, users do not need to select which electrodes to be activated, and do not need to select which activated electrodes are negative polarity or positive polarity. For example, if the electrical stimulation device 100 is equipped with 8 electrodes, these 8 electrodes can be 4 positive polarities and 4 negative polarities staggeringly arranged.

A pulse signal that is lower (e.g., 10K Hertz) than conventional electrical stimulation may be prone to cause discomfort such as the feeling of stabbing pain, or paresthesia to the user. In an embodiment of the present disclosure, the electrical stimulation signal is a high frequency (e.g., 500K Hertz) pulse signal, so it will not cause paresthesia to users, or just cause extremely slight paresthesia to users.

According to the embodiment of the present disclosure, the storage unit 160 may be a volatile memory (e.g., a random access memory (RAM)), or a non-volatile memory (e.g., flash memory), a read only memory (ROM), a hard drive, or any combination thereof. The storage unit 160 may be used for storing the files and data required for performing the electrical stimulation. According to an embodiment of the present disclosure, the storage unit 160 may be used for storing related information of the lookup table provided by the external control device 200.

Figure 4:
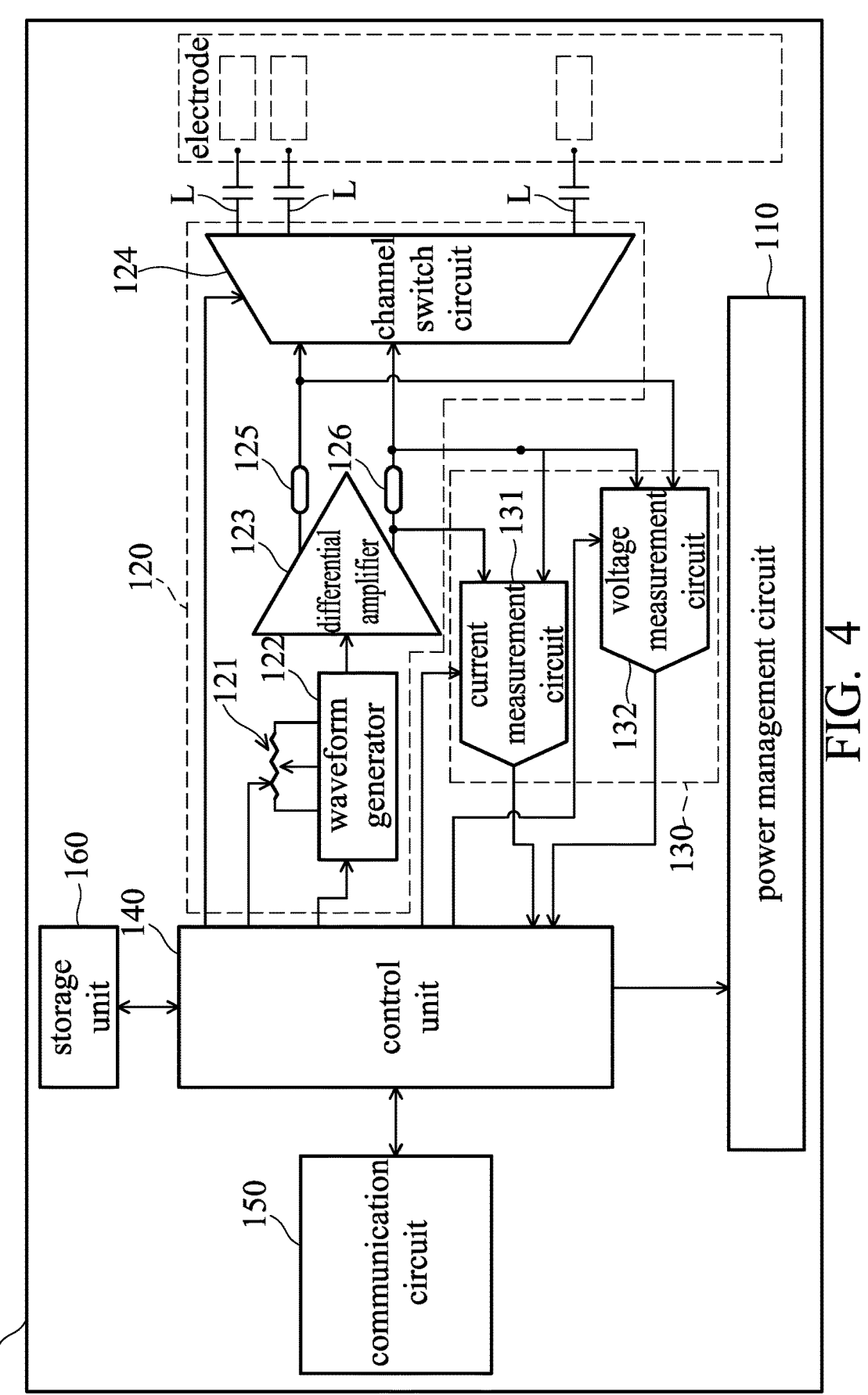
FIG. 4 is a detailed schematic diagram of an electrical stimulation device, according to an embodiment of the present disclosure.

FIG. 4 is a schematic diagram of an electrical stimulation device 100, according to an embodiment of the present disclosure. As shown in FIG. 4, the electrical stimulation signal generation circuit 120 may include a variable resistor 121, a waveform generator 122, a differential amplifier 123, a channel switch circuit 124, a first resistor 125, and a second resistor 126. The measurement circuit 130 may include a current measurement circuit 131 and a voltage measurement circuit 132. It should be appreciated that the schematic diagram shown in FIG. 4 is only for the convenience to explain the embodiments of the present disclosure, but the present disclosure is not limited to FIG. 4. The electrical stimulation device 400 may also include other elements, or other equivalent circuits.

As shown in FIG. 4, according to the embodiment of the present disclosure, the variable resistor 121 may be coupled to a serial peripheral interface (SPI) (not shown in the figure) of the control unit 140. The control unit 140 may transmit instructions to the variable resistor 121 via the SPI to adjust the resistance of the resistor 121, so as to adjust the amplitude of the electrical stimulation signal to be output. The waveform generator 122 may be coupled to a pulse width modulation (PWM) signal generator (not shown in the figure) of the control unit 140. The PWM signal generator may generate a square wave signal, and transmit the square wave signal to the waveform generator 122. After receiving the square wave signal generated by the PWM signal generator, the waveform generator 122 will convert the square wave signal into a sinusoidal wave signal, and transmit the sinusoidal wave signal to the differential amplifier 123. The differential amplifier 123 may convert the sinusoidal wave signal into a differential signal (i.e., the electrical stimulation signal output), and transmit the differential signal to the channel switch circuit 124 via the first resistor 125 and the second resistor 126. The channel switch circuit 124 may transmit the differential signal (i.e., the electrical stimulation signal output) to the electrode corresponding to each channel via the lead L in turn according to the instructions of the control unit 140.

As shown in FIG. 4, according to the embodiment of the present disclosure, the current measurement circuit 131 and the voltage measurement circuit 132 may be coupled to the differential amplifier 123, so as to obtain the current value and the voltage value of the differential signal (i.e., the electrical stimulation signal output). Besides, the current measurement circuit 131 and the voltage measurement circuit 132 may be used for measuring the voltage value and the current value on the tissues in the target area of the body of the user or the patient. In addition, the current measurement circuit 131 and the voltage measurement circuit 132 may be coupled to the input/output (I/O) interface (not shown in the figure) of the control unit 140, so as to receive the instructions from the control unit 140. According to the instructions of the control unit 140, the current measurement circuit 131 and the voltage measurement circuit 132 may adjust the current and the voltage of the electrical stimulation signal into a current value and a voltage value suitable for the control unit 140. For example, if the voltage value measured by the voltage measurement circuit 132 is ±10V, and the control unit 140 is suitable for processing a voltage value with 0-3 Volts, then the voltage measurement circuit 132 may decrease the voltage value to ±1.5V, and then increase the voltage value to 0-3V.

After adjusting the current value and the voltage value, the current measurement circuit 131 and the voltage measurement circuit 132 may transmit the adjusted electrical stimulation signal to the analog-to-digital convertor (ADC) (not shown in the figure) of the control unit 140. The ADC may take samples from the electrical stimulation signal for the control unit to perform follow-up computation and analysis.

According to an embodiment of the present disclosure, when performing electrical stimulation on the target area of the body of a patient, the user (medical personnel or the patient himself) may select an electrical stimulation level from among a plurality of electrical stimulation levels on the operation interface of the external control device 200. In the embodiment of the present disclosure, different electrical stimulation levels may correspond to different target energies. The target energy may be a set of default energy. When the user selects an electrical stimulation level, the electrical stimulation device 100 may find out how many millijoules of energy must be provided to the target area in order to perform the electrical stimulation, according to the target energy corresponding to the electrical stimulation level selected by the doctor or the user. According to the embodiment of the present disclosure, in the trial phase, a plurality of target energies corresponding to a plurality of electrical stimulation levels may be regarded as a first set of default target energy. According to the embodiment of the present disclosure, the first set of the default target energy (i.e., the target energies) may be a linear sequence, an arithmetic sequence, or a geometric sequence, but the present disclosure is not limited thereto.

According to an embodiment of the present disclosure, in the trial phase, the external control device 200 may be provided with a lookup table. In this embodiment, the first lookup table may record each of the electrical stimulation levels and the corresponding target energy. Therefore, according to the electrical stimulation level selected by the user, the external control device 200 may look up the lookup table, and obtain the target energy corresponding to the electrical stimulation level selected by the user from the first target energy set. After obtaining the target energy corresponding to the electrical stimulation level selected by the user, the external control device 200 will transmit the target energy to the electrical stimulation device 100. Thus, the electrical stimulation device 100 may perform electrical stimulation on the target area according to the target energy.

According to another embodiment of the present disclosure, the electrical stimulation device 100 may be provided with a built-in first lookup table (e.g., a first lookup table stored in the storage unit 160). In this embodiment, the first lookup table may record each of the electrical stimulation levels and the corresponding target energy. After the user has selected an electrical stimulation level from the external control device, the external control device 200 will transmit an instruction to inform the control unit 140 of the electrical stimulation device 100 what electrical stimulation level was selected by the user. Then, the control unit 140 may select the target energy that corresponds to the electrical stimulation level selected by the user from the first target energy set according to the built-in first lookup table. After obtaining the target energy, the electrical stimulation device 100 may perform electrical stimulation on the target area according to the selected target energy, until the corresponding first target energy value is transmitted to the target area and the time for the electrical stimulation ends. One round of electrical stimulation is thus completed.

According to another embodiment of the present disclosure, the communication circuit 150 may first obtain the electrical stimulation level selected by the user, and the first lookup table, from the external control device 200. In this embodiment, the first lookup table may record the electrical stimulation level and the corresponding target energy. Then, the control unit 140 selects the target energy that corresponds to the electrical stimulation level selected by the user from the first target energy set, according to the electrical stimulation level selected by the user and the first lookup table that are obtained from the external control device 200. After obtaining the target energy, the electrical stimulation device 100 may thus perform electrical stimulation on the target area according to the target energy.

According to the embodiment of the present disclosure, the users may select the electrical stimulation level from the lowest level (the lowest level of electrical stimulation corresponds to the lowest target energy in the first target energy set). After the electrical stimulation ends and the limited period passes, the next target energy may be selected from the first target energy set. Once the user finds the target energy that he/she prefers or that is more therapeutically effective, then the target energy may be regarded as a predetermined target energy, and the electrical stimulation level corresponding to the predetermined target energy may be regarded as a predetermined electrical stimulation level.

According to an embodiment of the present disclosure, in the permanent implantation phase, the external control device 200 (e.g., a controller of the external control device 200) may select a target energy upper bound and a target energy lower bound from the first target energy set according to the predetermined electrical stimulation level. Then, the external control device 200 (e.g., a controller of the external control device 200) may generate a second target energy set according to the target energy upper bound and the target energy lower bound. In this embodiment, the external control device 200 (e.g., a controller of the external control device 200) may generate a second lookup table according to the electrical stimulation level corresponding to each of the target energies in the second target energy set. The external control device 200 may transmit the second lookup table and the related parameter information to the electrical stimulation device 100. When the user is operating the external control device 200, the electrical stimulation device 100 may perform electrical stimulation according to the second lookup table and the related parameter information. According to an embodiment of the present disclosure, in the trial phase, an external electrical stimulation device (i.e., a non-implantable electrical stimulation device) is used to perform electrical stimulation according to the first target energy set in the first lookup table selected by the user. In the permanent phase, the electrical stimulation device 100 (i.e., an implantable electrical stimulation device) is used to perform electrical stimulation according to the second target energy set in the second lookup table selected by the user. In an embodiment of the present disclosure, the electrical stimulation device 100 performs electrical stimulation on the target area, until the corresponding second target energy value is transmitted to the target area and this round of electrical stimulation ends. One round of electrical stimulation is thus completed.

According to another embodiment of the present disclosure, in the permanent implantation phase, the electrical stimulation device 100 may select a target energy upper bound and a target energy lower bound from the first target energy set according to the predetermined electrical stimulation level. Then, the electrical stimulation device 100 may generate the second target energy set according to the target energy upper bound and the target energy lower bound. In this embodiment, the electrical stimulation device 100 may generate a second lookup table according to the second target energy set and the electrical stimulation level corresponding to each of the target energies in the second target energy set. The electrical stimulation device 100 may transmit the second lookup table and the related parameter information to the external control device 200. When the user is operating the external control device 200, the electrical stimulation device 100 may perform electrical stimulation according to the second lookup table and the related parameter information.

According to the embodiment of the present disclosure, the second target energy set may be a linear sequence, an arithmetic sequence, or a geometric sequence, but the present disclosure is not limited thereto. According to an embodiment of the present disclosure, the number of the target energies included by the first target energy set may be the same as the number of the target energies included by the second target energy set. According to another embodiment of the present disclosure, the number of the target energies included by the first target energy set may be different to the number of the target energies included by the second target energy set.

FIG. 5A illustrates the first target energy set, according to an embodiment of the present disclosure. FIG. 5B illustrates the second target energy set, according to an embodiment of the present disclosure. It should be appreciated that FIG. 5A and FIG. 5B are only for depicting an embodiment of the present disclosure, but the present disclosure is not limited to the first target energy set and the second target energy set in FIG. 5A and FIG. 5B.

As shown in FIG. 5A, the first lookup table may store the correspondence between electrical stimulation levels and the first target energies. The first target energy set may include the target energy X1-X10. The electrical stimulation levels Level 1(L1)-Level 10(L10) correspond to the target energies X1-X10, respectively, and the unit of the target energy is millijoule. In addition to the target energies, the electrical stimulation levels L1-L10 may further correspond to different current values or voltage values. In this embodiment, in the trial phase, when the predetermined electrical stimulation level selected by the user is L6 (the predetermined target energy is X6, accordingly), the predefined target energy upper bound is X8 and the target energy lower bound is X5. There is a target energy between the target energy upper bound X8 and the predetermined target energy X6, while there is no target energy between the target energy lower bound X5 and the predetermined target energy X6.

In the permanent implantation phase, after obtaining the target energy upper bound X8 and the target energy lower bound X5, the electrical stimulation device 100 or the external control device 200 may generate the second target energy set according to the target energy upper bound X8 and the target energy lower bound X5. As shown in FIG. 5B, the second target energy set may include target energies Y1-Y8, which correspond to the electrical stimulation levels L1-L8 of the external control device 200 respectively. Besides, in this embodiment, the lowest target energy Y1 of the second target energy set corresponds to the target energy lower bound X5, and the highest target energy Y8 corresponds to the target energy upper bound X8. In the permanent implantation phase, the electrical stimulation device 100 and the external control device 200 may perform operations of electrical stimulation according to the second target energy set.

According to the embodiment of the present disclosure, when corresponding to a predetermined electrical stimulation level in the trial phase, the first target energy set may include a target energy upper bound and a target energy lower bound. The target energy upper bound and the target energy lower bound will be brought into the permanent implantation phase. The target energy upper bound will be the highest target energy in the second target energy set, and the target energy lower bound will be the lowest target energy in the second target energy set (as shown in FIG. 5B).

As such, the user may perform the electrical stimulation in the permanent implantation phase using an energy intensity near the predetermined electrical stimulation level selected, thus the safety of the electrical stimulation is further assured.

According to an embodiment of the present disclosure, there is a first number of target energies between the target energy upper bound and the predetermined target energy, and there is a second number of target energies between the target energy lower bound and the predetermined target energy. According to an embodiment of the present disclosure, the first number (e.g., 2) is larger than the second number (e.g., 1) (as shown in FIG. 5). According to another embodiment of the present disclosure, the first number may be equivalent to the second number.

According to an embodiment of the present disclosure, the predetermined target energy is not included in the second target energy set (as shown in FIG. 5). According to another embodiment of the present disclosure, the predetermined target energy may be included in the second target energy set.

According to an embodiment of the present disclosure, the trial phase and the permanent implantation phase may both be further divided into a non-electrically-stimulating phase and an electrically-stimulating phase. In other words, the trial phase may include the non-electrically-stimulating phase and the electrically-stimulating phase, and the permanent implantation phase may also include the non-electrically-stimulating phase and the electrically-stimulating phase. The non-electrically-stimulating phase refers to when the electrical stimulation device 100 and the external control device 200 have just been turned on, or after the electrical stimulation device 100 and the external control device 200 have been connected, but the user has not yet initiated electrical stimulation. The electrical-stimulating phase refers to when the electrical stimulation device 100 has started providing electrical stimulation treatment. It should be noted that a method of how to calculate the tissue impedance value is applicable to the trial stage or the permanent implantation stage.

According to an embodiment of the present invention, before the electrical stimulation device 100 performs electrical stimulation on the target area, the control unit 140 of the electrical stimulation device 100 determines whether the signal quality of the electrical stimulation signal generated by the electrical stimulation signal generation circuit 120 meets a threshold standard. There are more detailed instructions below.

Figure 6:
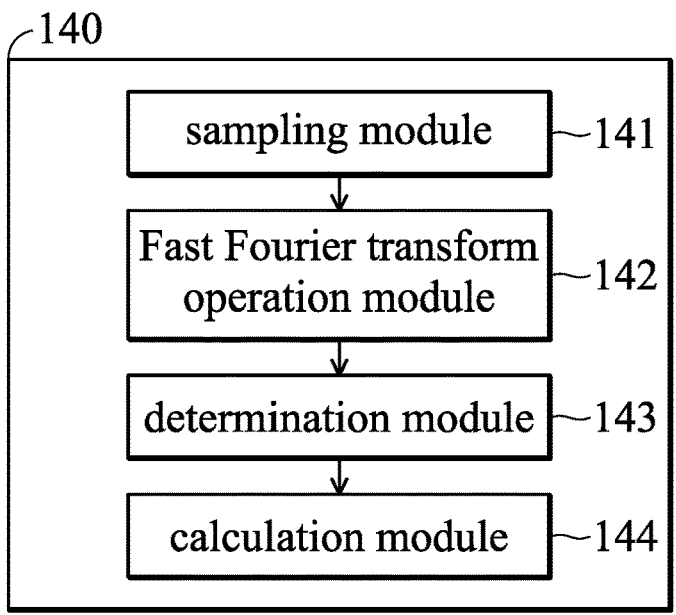
FIG. 6 is a block diagram of a control unit according to an embodiment of the present invention.

FIG. 6 is a block diagram of the control unit 140 according to an embodiment of the present invention. As shown in FIG. 6, the control unit 140 may comprise a sampling module 141, a Fast Fourier transform operation module 142, a determination module 143, and a calculation module 144. It should be noted that the block diagram shown in FIG. 6 is only for the convenience of explaining the embodiment of the present invention, but the present invention is not limited to FIG. 6. The control unit 140 may also comprise other elements. In the embodiment of the present invention, the sampling module 141, the fast Fourier transform operation module 142, the determination module 143 and the calculation module 144 may be implemented by hardware or software. Moreover, according to another embodiment of the present invention, the sampling module 141, the fast Fourier transform operation module 142, the determination module 143, and the calculation module 144 may also be independent from the control unit 140.

According to an embodiment of the present invention, when the control unit 140 of the electrical stimulation device 100 determines whether the signal quality of the electrical stimulation signal generated by the electrical stimulation signal generation circuit 120 meets the threshold standard, the sampling module 141 will first sample the electrical stimulation signal generated by the stimulation signal generating circuit 120 and sent it to the fast Fourier transform operation module 142 to perform a fast Fourier transform operation. More specifically, the sampling module 141 samples the voltage signal of the electrical stimulation signal, and the fast Fourier transform operation module 142 performs a fast Fourier transform operation on the sampled voltage signal. In addition, the sampling module 141 samples the current signal of the electrical stimulation signal, and the fast Fourier transform operation module 142 performs a fast Fourier transform operation on the sampled current signal. In the embodiment of the present invention, the sampling module 141 samples the electrical stimulation signal in a sampling period, and the sampling period indicates that the voltage signal and the current signal in a period of time in the pulses included in each duration $T_d$ are sampled, that is, sampling the electrical stimulation signal means sampling the pulse signal. According to an embodiment of the present invention, the sampling module 141 first samples the voltage signal of the electrical stimulation signal (for example, by taking 512 points), and then samples the current signal of the electrical stimulation signal (for example, by taking 512 points). However, the invention is not limited to the above sampling number or sampling order.

In an embodiment of the present invention, the sampling module 141 samples each pulse signal of the plurality of pulse signals. In another embodiment of the present invention, the sampling module 141 samples at least one of the plurality of pulse signals. For example, the sampling module 141 only samples one pulse signal among every two pulse signals, or the sampling module 141 samples only one pulse signal among every three pulse signals. In one embodiment of the present invention, the data of the adjacent sampled pulse signals may be applied to the unsampled pulse signal, however the present invention is not limited thereto. In other words, in an embodiment of the present invention, in one around of electrical stimulation (i.e., the transmission of the first target energy value or the second target energy value to the target area is completed), the sampling module 141 may sample at least one of a plurality of pulse signals at one or more times to obtain a corresponding tissue impedance value or tissue impedance values.

The determination module 143 will determine whether the signal quality of the electrical stimulation signal which has been processed by the fast Fourier transform operation meets the threshold standard. More specifically, the determination module 143 will determine whether a first frequency of the voltage signal that has been processed by the fast Fourier transform operation and a second frequency of the current signal which has been processed by the fast Fourier transform operation conform to a predetermined frequency, so as to determine whether the signal quality of the electrical stimulation signal meets the threshold standard. In other words, when the first frequency of the voltage signal that has been processed by the fast Fourier transform operation and the second frequency of the current signal which has been processed by the Fast Fourier transform operation conform to the predetermined frequency, the determination module 143 will determine that the signal quality of the electrical stimulation signal meets the threshold standard. When the first frequency of the voltage signal that has been processed by the fast Fourier transform operation and the second frequency of the current signal which has been processed by the fast Fourier transform operation do not conform to the predetermined frequency, the determination module 143 will determine that the signal quality of the electrical stimulation signal does not meet the threshold standard. According to one embodiment of the present invention, the predetermined frequency may be between 1K and 1M Hz. According to another embodiment of the present invention, the predetermined frequency may be between 480K and 520K Hz.

According to an embodiment of the present invention, when at least one of the first frequency and the second frequency does not conform to the predetermined frequency during the non-electrically-stimulating phase, the determination module 143 will determine whether a voltage value corresponding to the electrical stimulation signal is greater than or equal to a first predetermined voltage value (for example: 2 volts). If the voltage value is less than the first predetermined voltage value, the determination module 143 increases the voltage value of the electrical stimulation signal by a set value, and then the electrical stimulation signal is re-sampled. If the voltage value is greater than or equal to the first predetermined voltage value, the determination module 143 will report to the external control device 200 that the tissue impedance value cannot be calculated. According to an embodiment of the present invention, the set value may be a certain value between 0.1 and 0.4 volts, and the first predetermined voltage value may be a certain value between 1 and 4 volts, however the invention is not limited thereto. According to an embodiment of the present invention, an initial voltage value of the electrical stimulation signal is also a certain value between 0.1 and 0.4 volts. In this embodiment, when the first frequency or the second frequency does not conform to the predetermined frequency, the determination module 143 may first increase a value of a counter by one and determine whether the value of the counter is equal to a predetermined count value. When the value of the counter is equal to the predetermined count value, the determination module 143 will report to the external control device 200 that the tissue impedance value cannot by calculated. When the value of the counter is less than the predetermined count value, the determination module 143 determines whether a voltage value corresponding to the electrical stimulation signal is greater than or equal to a first predetermined voltage value. If the first frequency and the second frequency both conform to the predetermined frequency once before the value of the counter reaches the predetermined count value, the counter is reset to zero. According to an embodiment of the present invention, the predetermined count value may be any value between 10 and 30.

According to an embodiment of the present invention, in the non-electrically-stimulating phase, when the first frequency or the second frequency does not conform to the predetermined frequency, the determination module 143 will determine whether an average current value corresponding to the sampled electric stimulation signal is greater than or equal to a predetermined current value (for example: 2 mA). If the average current value is less than the predetermined current value, the determination module 143 increases the voltage value of the electrical stimulation signal by a set value. If the average current value is greater than or equal to the predetermined current value, the determination module 143 will perform the subsequent calculation of the electrical stimulation signal. According to an embodiment of the present invention, the set value may be a certain value between 0.1 and 0.4 volts, and the first predetermined voltage value may be a certain value between 1 and 4 volts, however the invention is not limited thereto. According to an embodiment of the present invention, an initial voltage value of the electrical stimulation signal is also a certain value between 0.1 and 0.4 volts.

According to an embodiment of the present invention, during the electrically-stimulating phase, when at least one of the first frequency and the second frequency does not conform to the predetermined frequency, the determination module 143 will re-sample the electrical stimulation signal and does not use the electrical stimulation signal which is sampled this time, or the external control device 200 can recognize that the electrical stimulation signal sampled this time is not used according to the determination result of the determination module 143. In the embodiment, when at least one of the first frequency and the second frequency does not conform to the predetermined frequency, the determination module 143 can use the electrical stimulation signal that met the threshold standard in the previous iteration to perform subsequent operations in the electrical stimulation. Alternatively, the external control device 200 can use the electrical stimulation signal that met the threshold standard in the previous iteration to perform subsequent operations in the electrical stimulation, according to the determination result of the determination module 143.

According to an embodiment of the present invention, when the determination module 143 determines that the signal quality of the electrical stimulation signal meets the threshold standard, the calculating module 144 will calculate an impedance value (i.e., a tissue impedance) corresponding to the sampled electrical stimulation signal value) to electrically stimulate a target area. There is a more detailed description provided below.

According to an embodiment of the present invention, when the determination module 143 determines that the signal quality of the electrical stimulation signal meets the threshold standard, the calculation module 144 extracts a first voltage sampling point corresponding to a maximum voltage value in each sampling period and a second voltage sampling point corresponding to a minimum voltage value, and subtracts the minimum voltage value from the maximum voltage value and divides the difference by 2 to generate an average voltage value, which can eliminate the background value. It should be noted that, as described above, the voltage measuring circuit 132 can increase the voltage value to a positive value according to the command of the control unit 140, so as to facilitate the processing by the control unit 140. Moreover, when the determination module 143 determines that the signal quality of the electrical stimulation signal meets the threshold standard, the calculation module 144 will extract a first current sampling point corresponding to a maximum current value and a second current sampling point corresponding a minimum current value in each sampling period value one of the s, and subtracts the minimum current value from the maximum current value and divides the difference by 2 to generate an average current value for eliminating background values. After obtaining the average voltage value and the average current value, the calculation module 144 obtains a total impedance value according to the average voltage value and the average current value and calculates the tissue impedance value according to the total impedance value. How to calculate the tissue impedance value based on the total impedance value is described below in detail. According to another embodiment of the present invention, if the background value is 0, the calculation module 144 may add the maximum voltage value and the minimum voltage value and then divide the sum by 2 to generate an average voltage value, and further add the maximum current value and the minimum current value and then divide the sum by 2 to generate the average voltage value.

According to another embodiment of the present invention, when the determination module 143 determines that the signal quality of the electrical stimulation signal meets the threshold standard, the sampling module 141 will sample all the peaks and valleys of the voltage signal of the electrical stimulation signal, and the calculation module 144 generates an average voltage value according to the values of all the voltage sampling points. For example, the calculation module 144 may average the peaks and valleys included in the 512 sampling points of the voltage signal sampled in each sampling period to generate the average voltage value. Moreover, the sampling module 141 samples all the peaks and valleys of the current signal of the electrical stimulation signal, and the calculation module 144 generates an average current value according to the values of all the current sampling points. For example, the calculation module 144 may average the peaks and valleys included in the 512 sampling points of the current signal sampled in each sampling period to generate the average current value. Then, the calculation module 144 obtains a total impedance value according to the average voltage value and the average current value and calculates the tissue impedance value according to the total impedance value. How to calculate the tissue impedance value based on the total impedance value is described below in detail.

According to an embodiment of the present invention, before the electrical stimulation device 100 performs electrical stimulation on the target area, e.g., in the non-electrically-stimulating phase, the electrical stimulation apparatus 100 calculates a tissue impedance value of the target area. According to an embodiment of the present invention, the electrical stimulation device 100 (such as the electrical stimulation device 100 shown in FIG. 2A) can calculate the tissue impedance value according to the impedance value of the lead and the impedance value of the electrical stimulation device 100 itself. According to another embodiment of the present invention, the electrical stimulation device 100 (such as the electrical stimulation device 100 shown in FIG. 2B) can calculate the tissue impedance value according to the impedance value of the electrical stimulation device 100 itself. There is a more detailed description provided below.

Figure 7:
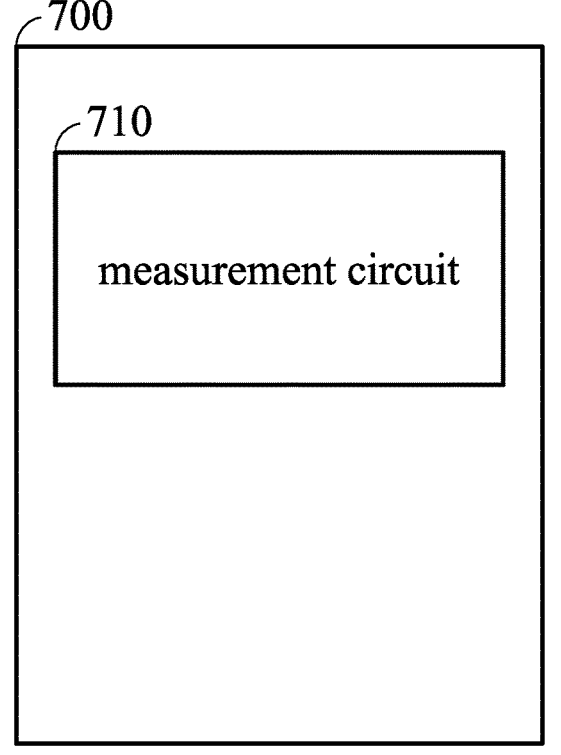
FIG. 7 is a block diagram of an impedance compensation device according to an embodiment of the present invention.

FIG. 7 is a block diagram showing an impedance compensation device 700 according to an embodiment of the present invention. As shown in FIG. 7, the impedance compensation device 700 may comprise a measurement circuit 710, however the invention is not limited thereto. The measurement circuit 710 can be used to measure an impedance value $Z_{Inner}$ of the electrical stimulation device 100 and an impedance value $Z_{lead}$ of the lead. According to an embodiment of the present invention, the impedance compensation device 700 (or the measurement circuit 710) may also comprise the related circuit structure shown in FIG. 4.

According to an embodiment of the present invention, when the measurement circuit 710 is to measure the electrical stimulation device 100 as shown in FIG. 2A, the measurement circuit 710 first provides a high-frequency environment. This frequency is the same as the frequency of the electrical stimulation signal which is provided for the electrical stimulation on the target area, for example 500 kHz. Then, the measurement circuit 710 measures a resistance value $R_{Lead}$, a capacitance value $C_{Lead}$, and an inductance value $L_{Lead}$ of the lead, and calculates the impedance value $Z_{Lead}$ of the lead under the high frequency signal according to at least one of the measured resistance value $R_{Lead}$, capacitance value $C_{Lead}$, and inductance value $L_{Lead}$. Moreover, the measurement circuit 710 measures a resistance value $R_{Inner}$, a capacitance value $C_{Inner}$, and an inductance value $L_{Inner}$ of the electrical stimulation device 100, and calculates the impedance value $Z_{Inner}$ of the electrical stimulation device 100 according to at least one of the measured resistance value $R_{Inner}$, capacitance value $C_{Inner}$, and inductance value $L_{Inner}$. In an embodiment of the present invention, the inductance value $L_{Inner}$ of the electrical stimulation device 100 may not be measured. The measurement circuit 710 writes the calculated impedance value $Z_{Lead}$ of the lead, and the impedance value $Z_{Inner}$ of the electrical stimulation device 100 into the firmware of the electrical stimulation device 100.

Figure 8A:
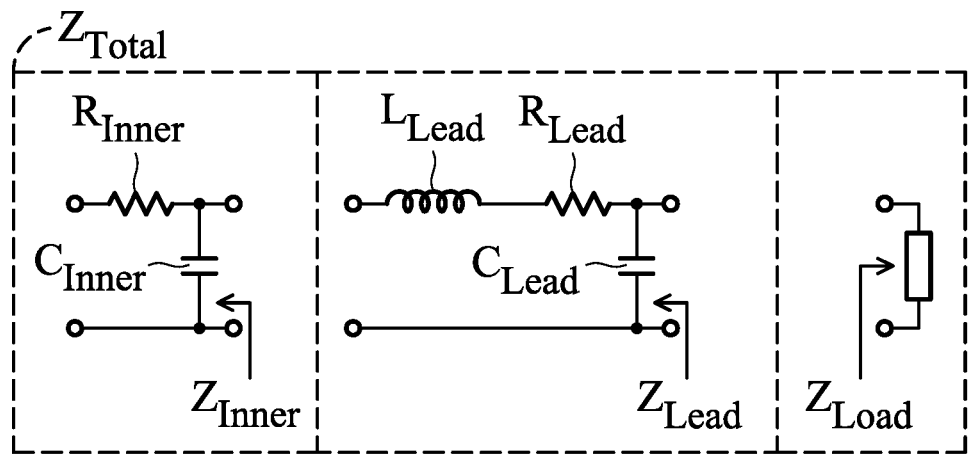
FIG. 8A is a schematic diagram of an impedance model according to an embodiment of the present invention.

When the electrical stimulation device 100 wants to calculate the tissue impedance value $Z_{Load}$ of the target area, the electrical stimulation device 100 deducts the impedance value $Z_{Lead}$ of the lead and the impedance value $Z_{Inner}$ of the electrical stimulation device 100 from the measured total impedance value $Z_{Total}$ to obtain the tissue impedance value $Z_{Load}$ of the target area, such as the impedance compensation model $Z_{Load} = Z_{Total} - Z_{Inner} - Z_{Lead}$ shown in FIG. 8A, however the present invention is not limited thereto. In the embodiment of the present invention, the total impedance value $Z_{Total}$ can be calculated by the calculation module 144 according to the current measured by the current measurement circuit 131 and the voltage measured by the voltage measuring circuit 132 (i.e., R=V/I). Since the calculation manner of the impedance value $Z_{Lead}$ of the lead and the impedance value $Z_{Inner}$ of the electrical stimulation device 100 can refer to Z=R+j (XL−XC), wherein R is resistance, XL is inductive reactance, and XC is capacitive reactance. They are well known to those skilled in the art, so the related description is omitted.

Figure 8B:
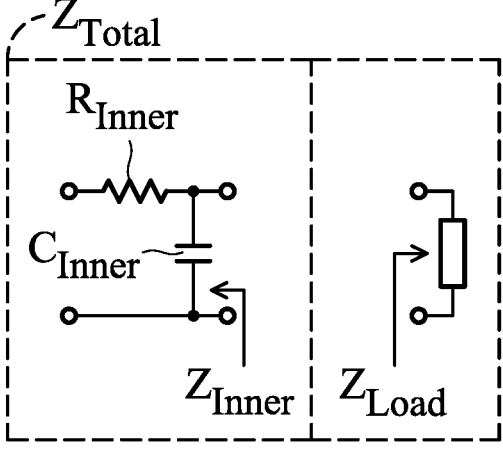
FIG. 8B is a schematic diagram of an impedance model according to another embodiment of the present invention.

According to another embodiment of the present invention, when the measurement circuit 710 is to measure the electrical stimulation device 100 as shown in FIG. 2B, the measurement circuit 710 first provides a high-frequency environment. The measurement circuit 710 measures a resistance value $R_{Inner}$, a capacitance value $C_{Inner}$, and an inductance value $L_{Inner}$ of the electrical stimulation device 100, and calculates the impedance value $Z_{Inner}$ of the electrical stimulation device 100 according to at least one of the measured resistance value $R_{Inner}$, the capacitance value $C_{Inner}$, and the inductance value $L_{Inner}$. In an embodiment of the present invention, the inductance value $L_{Inner}$ of the electrical stimulation device 100 may not be measured. The measurement circuit 710 writes the calculated impedance value $Z_{Inner}$ of the electrical stimulation device 100 into the firmware of the electrical stimulation device 100. When the electrical stimulation device 100 is to calculate the tissue impedance value $Z_{Load}$ of the target area, the electrical stimulation device 100 deducts the impedance value $Z_{Inner}$ of the electrical stimulation device 100 from the measured total impedance value $Z_{Total}$ to obtain the tissue impedance value $Z_{Load}$ of the target area, such as the impedance compensation model $Z_{Load} = Z_{Total} - Z_{Inner}$ shown in FIG. 8B, however the present invention is not limited thereto.

According to an embodiment of the present invention, the measurement circuit 710 can simulate a high-frequency environment according to an electrical stimulation frequency used by the electrical stimulation device 100. According to an embodiment of the present invention, the pulse frequency range of the high-frequency environment provided by the measurement circuit 710 can be in the range of 1 KHz to 1000 KHz. According to an embodiment of the present invention, the pulse frequency of the high-frequency environment provided by the measurement circuit 710 is the same as that of the electrical stimulation signal.

According to an embodiment of the present invention, the impedance compensation device 700 may be disposed in the external control device 200. According to another embodiment of the present invention, the impedance compensation device 700 may be disposed in the electrical stimulation device 100. That is, the high-frequency environment may be provided by the electrical stimulation device 100 or the external control device 200. Moreover, according to another embodiment of the present invention, the impedance compensation device 700 can also be an independent device (e.g., an impedance analyzer).

According to an embodiment of the present invention, the impedance compensation device 700 may be applied in a trial phase (i.e., the electrical stimulation device 100 is an external electrical stimulation device with a lead implanted in the body). According to an embodiment of the present invention, the impedance compensation device 700 can be applied in the permanent implantation stage (i.e., the electrical stimulation device 100 is an implantable electrical stimulation device, and the electrical stimulation device 100 can be implanted into the human body together with the lead).

According to an embodiment of the present invention, the impedance compensation device 700 can be applied before the production of the electrical stimulation device 100 (e.g., in the laboratory or factory terminal). In one embodiment, before the electrical stimulation device 100 is produced, the impedance compensation device 700 may first calculate the impedance value $Z_{Lead}$ of the lead and the impedance value $Z_{Inner}$ of the electrical stimulation device 100 and write the calculated impedance value $Z_{Lead}$ of the lead and the calculated impedance value $Z_{Inner}$ of the electrical stimulation device 100 into the firmware of the electrical stimulation device 100. In another embodiment, before the electrical stimulation device 100 is produced, the impedance compensation device 700 may first calculate the impedance value $Z_{Inner}$ of the electrical stimulation device 100 and write the calculated impedance value $Z_{Inner}$ of the electrical stimulation device 100 into the firmware of the electrical stimulation device 100. According to an embodiment of the present invention, the impedance compensation device 700 may also performs real-time compensation during the electrically-stimulating phase and the non-electrically-stimulating phase, that is, $Z_{Inner}$ and $Z_{Lead}$ can be measured each time an electrical stimulation signal is sent.

According to one embodiment of the present invention, after the electrical stimulation device 100 obtains the tissue impedance value $Z_{Load}$, the electrical stimulation device 100 transmits the tissue impedance value $Z_{Load}$ to the external control device 200. The external control device 200 will determine whether the tissue impedance value $Z_{Load}$ is within a predetermined range. During the electrically-stimulating phase, when the tissue impedance value $Z_{Load}$ is outside the predetermined range, the external control device 200 may indicate the electrical stimulation device 100 to terminate the electrical stimulation. In the electrically-stimulating phase, when the tissue impedance value $Z_{Load}$ is within the predetermined range, the external control device 200 may indicate the electrical stimulation device 100 to continue the electrical stimulation. According to another embodiment of the present invention, the electrical stimulation device 100 may also determine by itself whether the tissue impedance value $Z_{Load}$ is within a predetermined range. During the electrically-stimulating phase, when the tissue impedance value $Z_{Load}$ is outside the predetermined range, the electrical stimulation device 100 may terminate the electrical stimulation. In the electrically-stimulating phase, when the tissue impedance value $Z_{Load}$ is within the predetermined range, the electrical stimulation device 100 may continue the electrical stimulation. According to an embodiment of the present invention, the case in which the tissue impedance value is outside the predetermined range means that the electrical stimulation device 100 and the lead 210 are in an open circuit, and the case in which the tissue impedance value is within the predetermined range means that the electrical stimulation device 100 and the lead 210 are in normal electrical connection.

According to an embodiment of the present invention, an upper limit values of the predetermined range for the tissue impedance may be 2000 ohms, and a lower limit value of the predetermined range for the tissue impedance may be 70 ohms.

According to an embodiment of the present invention, after the electrical stimulation device 100 obtains a plurality of tissue impedance values $Z_{Load}$ (for example: three tissue impedance values $Z_{Load}$), the calculation module 144 will calculate the average tissue impedance value of the plurality of tissue impedance values and transmits the average tissue impedance value to the external control device 200. According to an embodiment of the present invention, the electrical stimulation device 100 may determine whether the average tissue impedance value is greater than the previous average tissue impedance value and whether the absolute value of the difference (i.e. absolute difference) between the average tissue impedance value and the previous average tissue impedance value is greater than a first predetermined percentage (for example: 3%, 5%, or 10%). When the average tissue impedance value is greater than the previous average tissue impedance value and the difference between the average tissue impedance value and the previous average tissue impedance value is greater than the first predetermined percentage, the electrical stimulation device 100 averages the average tissue impedance value and the previous average tissue impedance value to generate an average value and updates an output average tissue impedance value as this average value. When the average tissue impedance value is not greater than (i.e., equal to or less than) the previous average tissue impedance value or the difference between the average tissue impedance value and the previous average tissue impedance value is not greater than the first predetermined percentage, the electrical stimulation device 100 updates a tissue impedance temporarily stored for output as the average tissue impedance value.

Moreover, according to an embodiment of the present invention, the electrical stimulation device 100 may determine whether the absolute value of the difference between the output average tissue impedance value and the previous output average tissue impedance value is greater than a second predetermined percentage (for example: 3%, 5% or 10%). When the difference between the output average tissue impedance value and the previous output average tissue impedance vale is not greater than the second predetermined percentage, the external control device 200 indicates the electrical stimulation device 100 not to adjust an output current, wherein the output current refers to the current of the electrical stimulation signal generated by the electrical stimulation device 100. It should be noted that different output average tissue impedance values correspond to different output currents. When the output average tissue impedance value is greater, the output current is greater. In an embodiment of the present invention, the corresponding relationship between the output average tissue impedance value and the output current may be stored in a first look-up table or a second look-up table (not shown). When the difference between the output average tissue impedance value and the previous output average tissue impedance value is greater than the second predetermined percentage, the electrical stimulation device 100 determines whether the output average tissue impedance value is less than a predetermined impedance value (e.g., 2000 ohms). If the output average tissue impedance value is not less than (i.e., greater than or equal to) the predetermined impedance value, the electrical stimulation device 100 may determine not to adjust the output current. If the output average tissue impedance value is less than the predetermined impedance value, the electrical stimulation device 100 adjusts the output current according to the output average tissue impedance value.

For example, when the tissue impedance values obtained by the electrical stimulation device 100 for the first to third times are 290, 300, and 310 ohms, the electrical-stimulation device 100 may calculate the average tissue impedance value as 300 ohms; when the tissue impedance values obtained by the electrical stimulation device 100 for the fourth to sixth times are of 270, 280, 290 ohms, the (new) average tissue impedance value is 280 ohms. The average tissue impedance value at this time (280 ohms) is less than the previous average tissue impedance value (300 ohms), and the electrical stimulation device 100 updates the output average tissue impedance value as 280 ohms. When the tissue impedance values obtained by the electrical stimulation device 100 for the seventh to ninth times are obtains 340, 350, and 360 ohms, the average tissue impedance value is 350 ohms. The average tissue impedance value (350 ohms) at this time is greater than the previous average tissue impedance value (280 ohms), and the absolute value of the difference is greater than the first predetermined percentage (for example, 10%). Then, the electrical stimulation device 100 averages the current average tissue impedance value (350 ohms) and the previous average tissue impedance value (280 ohms) to generate an average value (315 ohms) and updates the output average tissue impedance value as the average value. Next, when the electrical stimulation device 100 determines that the absolute value of the difference between the output average tissue impedance value (315 ohms) and the previous output average tissue impedance value (280 ohms) is greater than the second predetermined percentage (for example: 5%), the electrical stimulation device 100 determines that the output average tissue impedance value (315 ohms) is less than the predetermined impedance value (e.g., 2000 ohms). The electrical stimulation device 100 adjusts the output current according to the current output average tissue impedance value (315 ohms).

In an embodiment of the present invention, the tissue impedance values, the average tissue impedance values, and the output average tissue impedance values can all be stored in the buffer region of the control unit 140 or the buffer region of the storage unit 120, however the present invention is not limited thereto.

According to an embodiment of the present invention, in the electrically-stimulating phase (i.e., when the electrical stimulation device 100 has provided electrical stimulation treatment), in order to make the measurement circuit 130 operate successfully, if the voltage of the electrical stimulation signal is greater than a second predetermined voltage value (for example, 7.5 volts), the electrical stimulation device 100 generates electrical stimulation signals of a first predetermined number (for example: 13) and performs a voltage reduction operation on electrical stimulation signals of a second predetermined number among the electrical stimulation signals of the first predetermined number. That is, the reducing voltages to the second predetermined voltage value is performed, and the electrical stimulation signals of the second predetermined number suffering the voltage reduction operation are used for the calculation of the subsequent tissue impedance value. The electrical stimulation signals, which do not suffer the voltage reduction operation, will not be used for the calculation of the subsequent tissue impedance. This operation is repeated. That is, after electrical stimulation signals of the first predetermined number are generated, electrical stimulation signals of the second predetermined number are generated, and the voltages are reduced to the second predetermined voltage value. Then, electrical stimulation signals of the first predetermined number are generated. For example, in the electrically-stimulating phase, if all the voltages of the electrical stimulation signals of front N times (for example, N=10, i.e. the 1st to 10th times) among the first predetermined number (for example: 13) are greater than the second predetermined voltage value (for example, 7.5 volts), these N electrical stimulation signals will not be used for the calculation of the subsequent tissue impedance value. The electrical stimulation device 100 performs the voltage reduction operation (for example, to 7.5 volts) only on electrical stimulation signals of the second predetermined number (for example: the 11th to 13th times) and the calculation of the subsequent tissue impedance is performed using the specific electrical stimulation signals which have suffered the voltage reduction operation.

In an embodiment of the present invention, the tissue impedance value is used to calculate the energy value of the electrical stimulation signal transmitted to the target area, and the calculation equation of the energy value transmitted by the electrical stimulation signal can be $E=0.5*I^2*Z_{Load}*PW*rate*t$, wherein E is the energy value, and the unit is Joule; 0.5 is a constant; I is the current, and the unit is ampere; PW is the pulse duration $T_d$ (that is, the duration $T_d$ in FIG. 3), and the unit is seconds; $Z_{Load}$ is the tissue impedance value, and the unit is ohm; rate is the pulse repetition frequency of the electrical stimulation signal, and the unit in Hertz; and t is the time for electrical stimulation, and the unit is seconds. In an embodiment of the present invention, the pulse width and the pulse frequency can be recorded in a look-up table stored in the storage unit 160 of the electrical stimulation device 100 and correspond to respective electrical stimulation levels. In another embodiment, the pulse width and pulse frequency can be recorded in a look-up table stored in the external control device 200 and correspond to the respective electrical stimulation levels, and the communication circuit 150 of the electrical stimulation device 100 can obtain the pulse width and pulse frequency from the external control device 200.

Since the tissue impedance value $Z_{Load}$ corresponding to the electrical stimulation signal sampled each time may vary, the energy value of the electrical stimulation signal sampled each time may vary accordingly. According to an embodiment of the present invention, in the electrically-stimulating phase, the calculation module 144 can calculate the energy value generated by the electrical stimulation signal to the target area to generate a total energy value and determine whether the total energy value has reached a target energy value. It should be noted that, if the sampling module 141 does not sample each pulse signal of a plurality of pulse signals, the total energy value still refers to the energy value generated by all the pulse signals to the target area. For example, in every two pulse signals, the sampling module 141 samples only one pulse signal, and the total energy value may be obtained by multiplying the energy value calculated for all the sampled pulse signals by 2.

When the total energy value has reached the target energy value, the electrical stimulation signal generation circuit 120 will stop providing any electrical stimulation signal to the target area, which means that the electrical stimulation device 100 will terminate the electrical stimulation. For example, assume the target energy value is 170 millijoules (mJ). If the energy value of the electrical stimulation signal output by the electrical stimulation device 100 is 100 mJ when the electrical stimulation signal corresponds to a first tissue impedance value $Z_{Load}$ and the energy value of the electrical stimulation signal output by the device 100 is 50 mJ when the next electrical stimulation signal corresponds to a second tissue impedance value $Z_{Load}$, the calculation module 144 can accumulate the energy value of the electrical stimulation signal to generate the total energy value (i.e., 100+50=150 mJ) and determines whether the total energy value has reached the target energy value (150<170, the target energy value has not been reached). When the total energy value has reached the target energy value, the electrical stimulation signal generation circuit 120 will stop providing any electrical stimulation signal to the target area.

Figure 9:
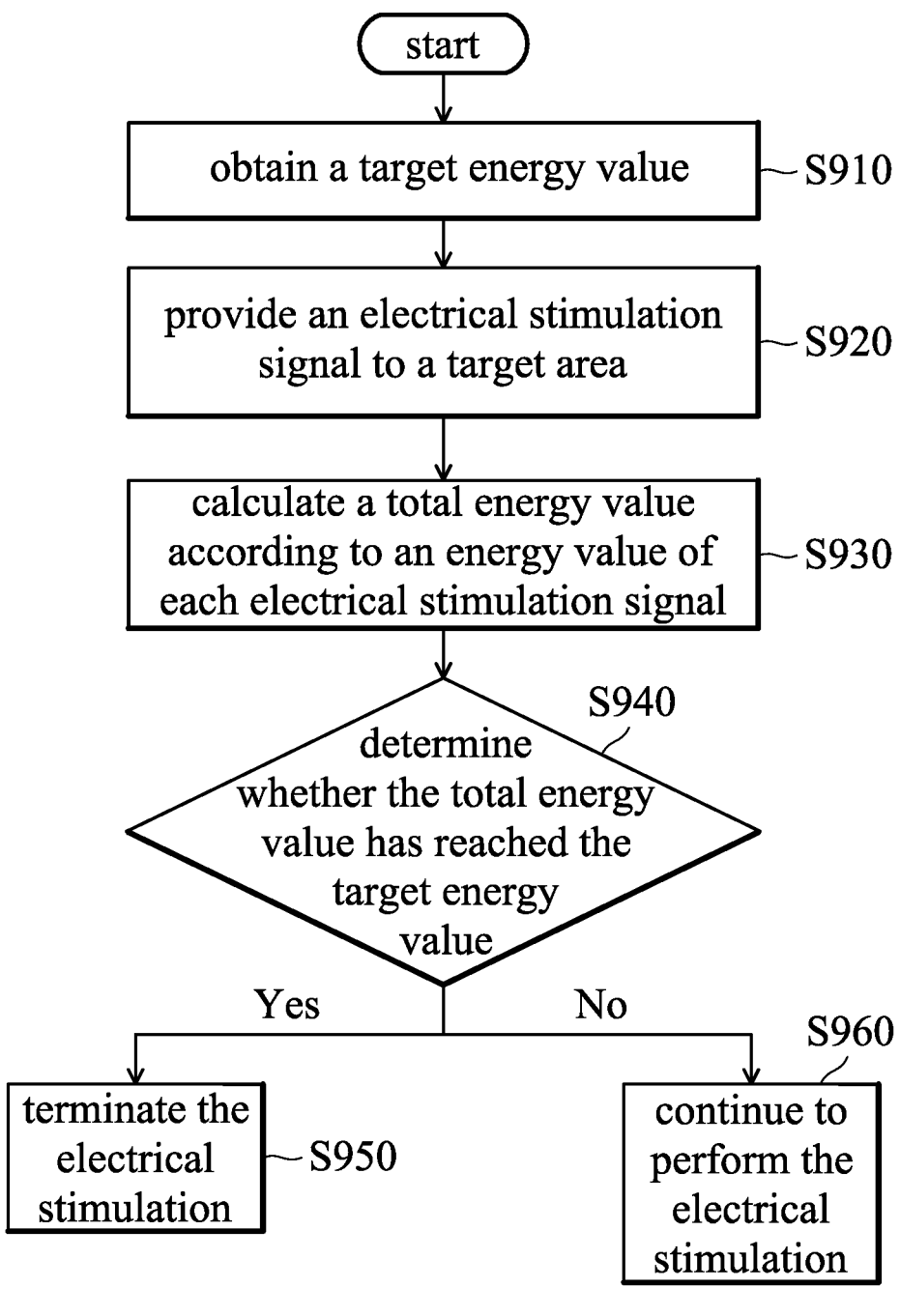
FIG. 9 is a flowchart of an electrical stimulation method according to an embodiment of the present invention.

FIG. 9 is a flowchart 900 of an electrical stimulation method according to an embodiment of the present invention. The flow diagram 900 of the electrical stimulation method is applicable to the electrical stimulation device 100. As shown in FIG. 9, in Step S910, the electrical stimulation device 100 obtains a target energy value.

In Step S920, the electrical stimulation device 100 provides an electrical stimulation signal to a target area.

In Step S930, the electrical stimulation device 100 calculates a total energy value according to the energy value transmitted by the electrical stimulation signal to the target area.

In Step S940, the electrical stimulation device 100 determines whether the total energy value has reached the target energy value.

If the total energy value has reached the target energy value, the method proceeds to Step S950. In Step S950, the electrical stimulation of the electrical stimulation device 100 is terminated.

If the accumulated energy value has not reached the target energy value yet, the method proceeds to Step S960. In Step S960, the electrical stimulation device 100 continues to perform the electrical stimulation.

According to an embodiment of the present invention, in step S940 of the electrical stimulation method, the electrical stimulation device 100 can calculate energy value of each electrical stimulation signal according to the current value of the electrical stimulation signal, the corresponding tissue impedance value, and a time parameter.

According to the electrical stimulation method proposed in the present invention, the electrical stimulation device 100 can calculate the energy value of the electrical stimulation signal according to the change of the tissue impedance value. When the total energy value of the electrical stimulation signal transmitted to the target area has reached the target energy value, the electrical stimulation is terminated. Therefore, the user can be prevented from suffering electrical stimulation for a long time, and the electrical stimulation can be more efficiently performed on the user according to the energy level.

Ordinal terms used in the claims, such as "first," "second," "third," etc., are only for convenience of explanation, and do not imply any precedence relation between one another.

The steps of the methods and algorithms provided in the present disclosure may be directly applied to a hardware and a software module or the combination thereof by executing a processor. A software module (including executing instructions and related data) and other data may be stored in a data memory, such as random access memory (RAM), flash memory, read-only memory (ROM), erasable programmable read only memory (EPROM), electrically erasable programmable read only memory (EEPROM), registers, hard drives, portable drives, CD-ROM, DVD, or any other computer-readable storage media format in the art. For example, a storage media may be coupled to a machine device, such as a computer/processor (denoted by "processor" in the present disclosure, for the convenience of explanation). The processor may read information (such as codes) from and write information to a storage media. A storage media may integrate a processor. An application-specific integrated circuit (ASIC) includes the processor and the storage media. A user apparatus includes an ASIC. In other words, the processor and the storage media are included in the user apparatus without directly connecting to the user apparatus. Besides, in some embodiments, any product suitable for computer programs includes a readable storage media, wherein the storage media includes codes related to one or more disclosed embodiments. In some embodiments, the computer program product may include packaging materials.

The above paragraphs are described with multiple aspects. Obviously, the teachings of the specification may be performed in multiple ways. Any specific structure or function disclosed in examples is only a representative situation. According to the teachings of the specification, it should be noted by those skilled in the art that any aspect disclosed may be performed individually, or that more than two aspects could be combined and performed.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An electrical stimulation method, applied to an implantable electrical stimulation device, comprising:

obtaining a target energy value;

providing an electrical stimulation signal to a target area during a treatment session;

accumulating an energy value of the electrical stimulation signal transmitted to the target area during the treatment session to generate a total energy value;

calculating the energy value of the electrical stimulation signal according to a detected tissue impedance value corresponding to the electrical stimulation signal;

determining whether the total energy value accumulated during the treatment session has reached the target energy value; and stopping providing the electrical stimulation signal to the target area when the total energy value has reached the target energy value, wherein the electrical stimulation signal comprises a plurality of pulse signals.

2. The electrical stimulation method as claimed in claim 1, wherein the electrical stimulation device samples at least one of the plurality of pulse signals to calculate the total energy value corresponding to the plurality of pulse signals.

3. The electrical stimulation method as claimed in claim 1, further comprising:

obtaining a voltage value of the electrical stimulation signal;

obtaining a current value of the electrical stimulation signal; and calculating the energy value of the electrical stimulation signal according to the voltage value and the current value of the electrical stimulation signal.

4. The electrical stimulation method as claimed in claim 1, further comprising:

obtaining a current value of the electrical stimulation signal; and calculating the energy value of the electrical stimulation signal according to the current value of the electrical stimulation signal and further according to a tissue impedance value corresponding to the electrical stimulation signal and a time parameter.

5. The electrical stimulation method as claimed in claim 4, wherein the time parameter comprises a pulse width and a pulse frequency.

6. The electrical stimulation method as claimed in claim 1, further comprising:

obtaining the target energy value, a pulse width, and a pulse frequency from an external control device through the electrical stimulation device.

7. The electrical stimulation method as claimed in claim 1, further comprising:

obtaining the target energy value, a pulse width, and a pulse frequency from the electrical stimulation device.

8. The electrical stimulation method as claimed in claim 1, wherein an intra-pulse frequency of the electrical stimulation signal is in a range from 480 KHz to 520 KHz.

9. The electrical stimulation method as claimed in claim 1, wherein a pulse frequency of the electrical stimulation signal is in a range of 0~1 KHz.

10. The electrical stimulation method as claimed in claim 1, wherein the step of accumulating the energy value of the electrical stimulation signal transmitted to the target area during the treatment session to generate the total energy value comprises:

in a sampling period, performing a first sampling on the electrical stimulation signal to obtain a first tissue impedance value;

calculating a first energy value of the electrical stimulation signal transmitted to the target area according to the first tissue impedance value;

in the sampling period, performing a second sampling on the electrical stimulation signal to obtain a second tissue impedance value;

calculating a second energy value of the electrical stimulation signal transmitted to the target area according to the second tissue impedance value;

accumulating the first energy value and the second energy value to generate the total energy value.

11. An implantable electrical stimulation device comprising:

an electrical stimulation signal generation circuit providing an electrical stimulation signal to a target area during a treatment session; and a calculation module configured to obtain a target energy value, accumulate an energy value of the electrical stimulation signal transmitted to the target area during the treatment session to generate a total energy value, calculate the energy value of the electrical stimulation signal according to a detected tissue impedance value corresponding to the electrical stimulation signal and determine whether the total energy value accumulated during the treatment session has reached the target energy value, wherein when the total energy value has reached the target energy value, the electrical stimulation signal generation circuit stops providing the electrical stimulation signal to the target area, wherein the electrical stimulation signal comprises a plurality of pulse signals.

12. The implantable electrical stimulation device as claimed in claim 11, wherein the electrical stimulation device samples at least one of the plurality of pulse signals to calculate the total energy value corresponding to the plurality of pulse signals.

13. The implantable electrical stimulation device as claimed in claim 11, wherein the calculation module is further configured to obtain a voltage value of the electrical stimulation signal, obtain a current value of the electrical stimulation signal, and calculate the energy value of the electrical stimulation signal according to the voltage value and the current value of the electrical stimulation signal.

14. The implantable electrical stimulation device as claimed in claim 11, wherein the calculation module is further configured to obtain a current value of the electrical stimulation signal and calculate the energy value of the electrical stimulation signal according to the current value of the electrical stimulation signal and further according to a tissue impedance value corresponding to the electrical stimulation signal and a time parameter.

15. The implantable electrical stimulation device as claimed in claim 14, wherein the time parameter comprises a pulse width and a pulse frequency.

16. The implantable electrical stimulation device as claimed in claim 11, further comprising a communication circuit, wherein the communication circuit obtains the target energy value, a pulse width, and a pulse frequency from an external control device.

17. The implantable electrical stimulation device as claimed in claim 11, further comprising a storage unit, wherein the storage unit stores a lookup table, and the calculation module is configured to obtain the target energy value, a pulse width, and a pulse frequency from the storage unit.

18. The implantable electrical stimulation device as claimed in claim 11, wherein an intra-pulse frequency of the electrical stimulation signal is in a range from 480 KHz to 520 KHz.

19. The implantable electrical stimulation device as claimed in claim 11, wherein a pulse frequency of the above electrical stimulation signal is in a range of 0~1 KHz.

20. The implantable electrical stimulation device as claimed in claim 11, wherein in a sampling period, the calculation module is configured to perform a first sampling on the electrical stimulation signal to obtain a first tissue impedance value and perform a second sampling on the electrical stimulation signal to obtain a second tissue impedance value, the calculation module is configured to calculate a first energy value of the electrical stimulation signal transmitted to the target area according to the first tissue impedance value and calculate a second energy value of the electrical stimulation signal transmitted to the target area according to the second tissue impedance value, and the calculation module is configured to accumulate the first energy value and the second energy value to generate the total energy value.

21. A non-transitory computer-readable storage medium storing one or more instructions and cooperating with an implantable electrical stimulation device, wherein when the one or more instructions are executed by an electrical stimulation device, the electrical stimulation device executes a plurality of steps comprising:

obtaining a target energy value;

providing an electrical stimulation signal to a target area during a treatment session;

accumulating an energy value of the electrical stimulation signal transmitted to the target area during the treatment session to generate a total energy value;

calculating the energy value of the electrical stimulation signal according to a detected tissue impedance value corresponding to the electrical stimulation signal;

determining whether the total energy value accumulated during the treatment session has reached the target energy value; and stopping providing the electrical stimulation signal to the target area when the total energy value has reached the target energy value, wherein the electrical stimulation signal comprises a plurality of pulse signals.

22. The non-transitory computer-readable storage medium as claimed in claim 21, wherein the electrical stimulation device samples at least one of the plurality of pulse signals to calculate the total energy value corresponding to the plurality of pulse signals.

23. The non-transitory computer-readable storage medium as claimed in claim 21, wherein the plurality of steps executed by the electrical stimulation device further comprise:

obtaining a voltage value of the electrical stimulation signal;

obtaining a current value of the electrical stimulation signal; and calculating the energy value of the electrical stimulation signal according to the voltage value and the current value of the electrical stimulation signal.

24. The non-transitory computer-readable storage medium as claimed in claim 21, wherein the plurality of steps executed by the electrical stimulation device further comprise:

obtaining a current value of the electrical stimulation signal; and calculating the energy value of the electrical stimulation signal according to the current value of the electrical stimulation signal and further according to a tissue impedance value corresponding to the electrical stimulation signal and a time parameter.

25. The non-transitory computer-readable storage medium as claimed in claim 24, wherein the time parameter comprises a pulse width and a pulse frequency.

26. The non-transitory computer-readable storage medium as claimed in claim 21, wherein the plurality of steps executed by the electrical stimulation device further comprise:

obtaining the target energy value, a pulse width, and a pulse frequency from the electrical stimulation device.

27. The non-transitory computer-readable storage medium as claimed in claim 21, wherein a pulse frequency of the above electrical stimulation signal is in a range of 0~1 KHz.

28. The non-transitory computer-readable storage medium as claimed in claim 21, wherein the plurality of steps executed by the electrical stimulation device further comprise:

in a sampling period, performing a first sampling on the electrical stimulation signal to obtain a first tissue impedance value;

calculating a first energy value of the electrical stimulation signal transmitted to the target area according to the first tissue impedance value;

in the sampling period, performing a second sampling on the electrical stimulation signal to obtain a second tissue impedance value;

calculating a second energy value of the electrical stimulation signal transmitted to the target area according to the second tissue impedance value;

accumulating the first energy value and the second energy value to generate the total energy value.

* * * * *